(12) United States Patent
Yoshiyama

(10) Patent No.: US 9,051,456 B2
(45) Date of Patent: Jun. 9, 2015

(54) AGENT FOR DRUG CLEARANCE AND ACCELERATOR FOR DRUG CLEARANCE

(75) Inventor: Yuji Yoshiyama, Kamakura (JP)

(73) Assignee: SEIKAGAKU CORPORATION, Tokyo (JP)

( * ) Notice: Subject to any disclaimer, the term of this patent is extended or adjusted under 35 U.S.C. 154(b) by 223 days.

(21) Appl. No.: 11/814,976

(22) PCT Filed: Jan. 27, 2006

(86) PCT No.: PCT/JP2006/301340
§ 371 (c)(1),
(2), (4) Date: Jul. 27, 2007

(87) PCT Pub. No.: WO2006/080449
PCT Pub. Date: Aug. 3, 2006

(65) Prior Publication Data
US 2008/0167267 A1    Jul. 10, 2008

(30) Foreign Application Priority Data

Jan. 27, 2005  (JP) .................... 2005-019835
Jan. 27, 2005  (JP) .................... 2005-019836

(51) Int. Cl.
*A61K 31/728*  (2006.01)
*C08L 5/08*  (2006.01)
*A61K 31/575*  (2006.01)

(52) U.S. Cl.
CPC ............... *C08L 5/08* (2013.01); *A61K 31/575* (2013.01); *A61K 31/728* (2013.01)

(58) Field of Classification Search
CPC .................................................. A61K 31/728
USPC .......................................................... 514/54
See application file for complete search history.

(56) References Cited

U.S. PATENT DOCUMENTS

| | | | |
|---|---|---|---|
| 5,639,738 A * | 6/1997 | Falk et al. ................ | 514/54 |
| 2004/0254143 A1 * | 12/2004 | Mastradonato et al. ....... | 514/54 |

FOREIGN PATENT DOCUMENTS

| | | | |
|---|---|---|---|
| EP | 0 444 492 A1 | 9/1991 | |
| JP | 61-024510 A | 2/1986 | |
| JP | 09-194328 A | 7/1997 | |
| JP | 9-508898 T | 9/1997 | |
| JP | 10182390 A | 7/1998 | |
| JP | 10-245329 A | 9/1998 | |
| JP | 2001-212573 A | 8/2001 | |
| JP | 2001-247446 A | 9/2001 | |
| JP | 2001-270809 * | 10/2001 | ............... A61K 7/02 |
| JP | 2001-270809 A | 10/2001 | |
| JP | 2002029950 A | 1/2002 | |
| JP | 2003-300811 A | 10/2003 | |
| JP | 2005-29484 A | 2/2005 | |
| WO | 00/56344 A1 | 9/2000 | |
| WO | 2007/022734 A1 | 3/2007 | |

OTHER PUBLICATIONS

Luo, Yi and Prestwich, Glenn D., Bioconjugate Chemistry "Synthesis and Selective Cytotoxicity of a Hyaluronic Acid-Antitumor Bioconjugate" (1999), vol. 10, pp. 755-763.*
Morimoto, K. et al., Pharmaceutical Research "Effects of Viscous Hyaluronate-Sodium Solutions on the Nasal Absorption of Vasopressin and an Analogue" (1991), vol. 8, issue 4, pp. 471-474.*
Brutsche, M. H. et al., The Lancet "Comparison of pharmacokinetics and systemic effects of inhaled fluticasone propionate in patients with asthma and healthy volunteers: a randomised crossover study", vol. 356, pp. 556-561, published Aug. 2000.*
Forteza, R. et al., FASEB Journal, "Hyaluronan serves a novel role in airway mucosal host defense", vol. 15, pp. 2179-2186, published Oct. 2001.*
Ayres, J.G. et al., Eur. Respir. J., "High dose fluticasone propionate, 1 mg daily, versus fluticasone propionate, 2 mg daily, or budesonide, 1.6 mg daily, in patients with chronic severe asthma", 1995, vol. 8, pp. 579-586.*
Uematsu, H. et al., "Synthetic research on the method for oral cavity care and its preventive effect on the respiratory tract infection for aged people. Research on the effect of the mouth-rinsing medicine containing the moistening agent on the dry oral cavity in care-requiring aged people", J-EAST abstract, 2004; Accession No. 05A0411129.*
Yokota, M. et al., Otorhinolaryngology, "Evaluation of Wash Solutions for Removing Drug Residues in the Mouth after Steroid Inhalation", 2003, vol. 46, No. 1, pp. 15-19, human translation and original document.*
Grunsven, P. van et al., Respiratory Medicine, "Short- and long-term effiacy of fluticasone propionate in subjects with early signs and symptoms of chronic obstructive pulmonary disease", 2003, vol. 97, pp. 1303-1312.*
Yokota, M. et al. "Evaluation of Wash Solutions for Removing Drugs in the Mouth After Steroid Inhalation" Jibiinkoukatenbou (Oto-Rhino-Laryngology), Aug. 15, 2003, pp. 15-19.
Japanese Office Action dated Nov. 22, 2011 issued by the Japanese Patent Office in counterpart Japanese Patent Application No. 2007-500602.
Database WPI Week 200314 Thomson Scientific, London, GB; AN 2003-145573 XP002597043 & KR 2002 071 386 A (Since BIO) Sep. 12, 2002 * abstract *.
Database WPI Week 200475 Thomson Scientific, London, GB; AN 2004-759508 XP002597033 & JP 2004 277293 A (Pola Chem Ind Inc) Oct. 7, 2004 * abstract *.
Database WPI Week 200418 Thomson Scientific, London, GB ; AN 2004-184802 XP002597035 & JP 2004 026773 A (Utena KK) Jan. 29, 2004 * abstract *.
"Tear film-protecting and -restoring eyewash compositions contains hyaluronic acid as the effective component and other thickening agents, and their use" Derwent, Sep. 11, 2002, XP002238665 * abstract *.

(Continued)

*Primary Examiner* — Layla Bland
*Assistant Examiner* — Bahar Craigo
(74) *Attorney, Agent, or Firm* — Sughrue Mion, PLLC

(57) ABSTRACT

An agent for eliminating a drug and an accelerator for eliminating a drug which comprise hyaluronic acid or a salt thereof.

1 Claim, 3 Drawing Sheets

(56) References Cited

OTHER PUBLICATIONS

Wieczorowska K et al : "Protective Effect of Hyaluronic Acid Against Peritoneal Injury" Peritoneal Dialysis International, Pergamon Press, New York, NY, US, vol. 15, No. 1, Jan. 1, 1995, pp. 81-83, XP000614160 ISSN : 0896-8608 * p. 82, left-hand column, paragraph 3 *.

Artola A et al : "Protective Properties of Vicoelastic Substances (Sodium Hyaluronate and 2% Hydroxymethylcellulose) Against Experimental Free Radical Damage to the Corneal Endothelium" Cornea, Masson Publ, US LNKD-DOI : 10.1097/00003226-199303000-00003, vol. 12, No. 2, Jan. 1, 1993, pp. 109-114, XP008005337 ISSN : 0277-3740 * p. 109, left-hand column, paragraph 1 *.

Database Meadline [Online] US National Library of Medicine (NLM), Bethesda, MD, US; May 2005, Yildirim Altan et al : "Early effect of exogenous Na hyaluronate on mucociliary clearance." XP002597036 Database accession No. NLM16011128 * abstract * & American Journal of Rhinology May-Jun 2005 LNKD— PUBMED : 16011128, vol. 19, No. 3, May 2005, pp. 244-247, ISSN : 1050-6586.

Extended European Search Report dated Sep. 6, 2010 issued in corresponding European Application No. 06712506.2.

Yokoyama et al., "[Effect of mouth wash on the removing fluticasone propionate delivered by dry powder inhaler in mouth].", Database Medline [Online], US National Library of Medicine (Nlm), Database accession no. NLM11265118; & Yakugaku Zasshi, Journal of the Pharmaceutical Society of Japan, Mar., 2001, vol. 121, No. 3, 1 page.

Office Action dated Jan. 23, 2015 issued by the European Patent Office in corresponding European Application No. 06 712 506.2.

\* cited by examiner

AGENT FOR DRUG CLEARANCE AND ACCELERATOR FOR DRUG CLEARANCE

TECHNICAL FIELD

The present invention relates to an agent for eliminating a drug and an accelerator for eliminating a drug which comprise hyaluronic acid (to be referred to as "HA" hereinafter) or a salt thereof.

BACKGROUND OF THE INVENTION

The following describes background of the present invention.

It is disclosed in Patent Reference 1 that artificial saliva and the like for improving various symptoms caused by oral dryness, which comprise HA or a pharmaceutical acceptable salt thereof.

It is disclosed in Patent Reference 2 that composition for preventing dryness, which comprises a mixture of water with moisture keeping agents such as saccharides and a surfactant.

It is disclosed in Patent Reference 3 that a therapeutic composition which comprises an aqueous solution of at least one polymer and at least one electrolyte, and also describes a saliva substitute agent which comprises said composition.

It is disclosed in Patent Reference 4 that use of a pharmaceutical composition which comprises HA having an average molecular weight of from 800,000 to 4,000,000 as the active ingredient, for treating and preventing inflammation of oral cavity, oral cavity sanitation and the like.

However, it is neither disclosed nor suggested in any of there references that the use of HA or a salt thereof for eliminating drugs and accelerating elimination of drugs.

On the other hand, there is a case which requires elimination of a drug unintentionally contacted or adhered, or a case in which once intentionally contacted or adhered and becomes necessary to eliminate the drug thereafter. For example, when a drug accidentally got into the eye, adhered to the skin, got into the mouth or was swallowed, it is necessary to eliminate the drug as much as possible and also efficiently. Additionally, for example, in the case of steroid inhalant and the like which are used for the treatment of bronchial asthma and the like, it is necessary to eliminate the steroid drug remained in the oral cavity after its administration, in order to prevent its side effects.

Patent Reference 1: International Publication No. 00/56344
Patent Reference 2: JP-A-61-24510
Patent Reference 3: JP-T-9-508898
Patent Reference 4: European Patent No. 444-492

DISCLOSURE OF THE INVENTION

Problems to be Solved by the Invention

The object of the present invention is providing an agent and an accelerator for eliminating the aforementioned drugs as much as possible and also efficiently.

Means for Solving the Problems

The inventors of the present invention have conducted intensive studies to solve the aforementioned problems and found as a result that HA or a salt thereof is markedly effective for eliminating drugs and accelerating elimination of drugs. Thus, the present invention is accomplished.

Namely, the present invention provides an agent for eliminating a drug which comprises HA or a salt thereof (to be referred to as "an agent for eliminating a drug of the present invention" hereinafter). Also, the present invention provides an accelerator for eliminating a drug which comprises HA or a salt thereof (to be referred to as "accelerator of the present invention" hereinafter). In the following, the agent for eliminating a drug of the present invention and accelerator of the present invention may also be generally referred to as "preparation of the present invention". It is preferable to use the preparation of the present invention as an agent for eliminating a drug or an accelerator for eliminating a drug from living bodies, and it is more preferable to use it as an agent for eliminating a drug or an accelerator for eliminating a drug from an animal tissue. Also, it is preferable that this animal tissue is an epithelial tissue. Additionally, it is preferable that this epithelial tissue is mucosal epithelium, and it is preferable that the mucosal epithelium is originated from the inside of a digestive organ. Also, it is preferable that the digestive organ is the oral cavity. Also, it is preferable that the drug to be eliminated is a medicament or a drug which has the steroid nucleus. Additionally, it is preferable that the accelerator of the present invention is used prior to the application of the drug to be eliminated.

Effect of the Invention

The preparation of the present invention is markedly useful, since it can eliminate the drug to be eliminated conveniently, efficiently and in a large amount and also can accelerate the elimination. Additionally, the preparation of the present invention is markedly useful also from the viewpoint that HA as its active ingredient has already been on the market as pharmaceutical preparations, food and the like, and its safety is shown in the Examples which are described later.

BEST MODE FOR CARRYING OUT THE INVENTION

Figure 1A:
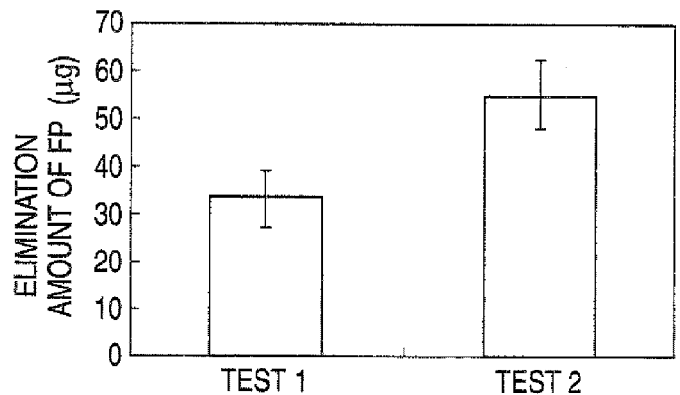
FIG. 1 is a graph which shows the amount of FP eliminated from inside of the oral cavity, and its comparison between each test.

In the following, the present invention is described in detail based on the best mode for carrying out the present invention
<1> Component of the Preparation of the Present Invention The preparation of the present invention is an agent for eliminating a drug or an accelerator for eliminating a drug which comprise HA or a salt thereof.

The origin of HA or a salt thereof which can be used as the component of the present invention is not particularly limited, and HA separated and purified from a cockscomb, an umbilical cord, an HA-producing microorganism and the like can be used. Additionally, its purity is not also particularly limited and can be appropriately selected according to the substance from which the drug should be eliminated or the substance in which elimination of the drug therefrom should be accelerated, situations, objects and the like. For example, when it is made into an agent for eliminating a drug or an accelerator for eliminating a drug for substances such as living body tissues in which high sterility, cleanness and the like are required, it is preferable to use HA which is purified to a high purity and does not substantially contain medically unacceptable substances (e.g., endotoxin and the like). Also, when it is made into an agent for eliminating a drug or an accelerator for eliminating a drug from the inside of digestive organs including the oral cavity, the skin and the like, although it is preferable to use HA which is purified to a high purity, there is a case in which the component having a slightly low purity can be used without problems. Additionally, when it is made into an agent for eliminating a drug or an accelerator for eliminating a drug for substances other than the living bodies, although it is preferable to use HA which is purified to a high purity as a matter of course, but HA having low purity can also be used in response to the objects, situations and the like.

Furthermore, with regard to the "salt of HA", it also is not particularly limited and can be appropriately selected according to the substance from which the drug should be eliminated or the substance in which elimination of the drug therefrom should be accelerated, situations, objects and the like. For example, when it is made into an agent for eliminating a drug or an accelerator for eliminating a drug for tissues in the living body and the like, a medically acceptable salt can be selected. The salt of HA includes, for example, salts with inorganic bases such as alkali metal salts (sodium salt, lithium salt, potassium salt and the like), alkaline earth metal salts, ammonium salts and the like, and salts with organic bases such as diethanolamine salt, cyclohexylamine salt, an amino acid salt and the like can be cited. Sodium salt is particularly preferable.

Weight-average molecular weight of the HA or a salt thereof which can be used as the component the preparation of the present invention is not also particularly limited and can be appropriately selected according to the objects and the like. For example, it can be a range of from 50,000 to 5,000,000 as the weight-average molecular weight of the HA or a salt thereof. Particularly, a range from 100,000 to 4,000,000 are preferable, a range from 200,000 to 3,000,000 are more preferable, a range from 300,000 to 2,500,000 are more preferable, a range from 300,000 to 2,000,000 are more preferable, a range from 300,000 to 1,500,000 are more preferable, a range from 300,000 to 1,300,000 are more preferable, a range from 400,000 to 1,300,000 are more preferable, a range from 500,000 to 1,300,000 are more preferable, a range from 500,000 to 1,200,000 are more preferable, a range from 500,000 to 1,100,000 are more preferable, a range from 500,000 to 1,000,000 are more preferable, and a range from 500,000 to 900,000 are particularly preferable. In this connection, the weight-average molecular weight of the HA or a salt thereof to be used in the present invention can be calculated based on the formula of Laurent et al. (*Biochim. Biophys. Acta,* 42, 476 (1960)), by measuring its limiting viscosity in accordance with The Pharmacopoeia of Japan, 13$^{th}$ revised edition: General Test Methods, Item 36 Viscosity Measurement.

When such HA or a salt thereof is used, it can be made into the preparation of the present invention which has markedly excellent effects.

<2> Dosage Forms and the Like of the Preparation of the Present Invention

Dosage forms and the like of the preparation of the present invention are not particularly limited, as long as they contain HA or a salt thereof and the drug elimination effect and drug elimination accelerating effect are shown. For example, these may be made into preparations in the state of solutions containing HA or a salt thereof or made into powders, granules and the like solid preparations which are dissolved when used. Also, when it is used for the acceleration of drug elimination in the oral cavity, it may be made into candies, Gumi preparations, jellies, troches and the like dosage forms. Additionally, when it is provided as preparations in the state of solution for example, it may be provided in the frozen state or may be provided directly as the solution.

Concentration of HA or a salt thereof in the preparation of the present invention is also not particularly limited and can be appropriately selected according to the objects and the like. For example, it can be a range of from 0.01 to 4% (w/v) in the state of solution Particularly, approximately from 0.01 to 3% (w/v) is preferable, approximately from 0.01 to 2% (w/v) is more preferable, approximately from 0.01 to 1% (w/v) is more preferable, approximately from 0.01 to 0.8% (w/v) is more preferable, approximately from 0-04 to 0.7% (w/v) is more preferable, approximately from 0.05 to 0.6% (w/v) is more preferable, approximately from 0.06 to 0.5% (w/v) is more preferable, approximately from 0.07 to 0.5% (w/v) is more preferable, approximately from 0.08 to 0.5% (w/v) is more preferable, approximately from 0.09 to 0.5% (w/v) is more preferable approximately from 0.1 to 0.5% (w/v) is more preferable, and approximately from 0.1 to 0.4% (w/v) is particularly preferable.

Circulation storage, use and the like of the preparation of the present invention can be carried out by filling it in an ampoule, vial, bottle, syringe or the like appropriate container.

Conventionally known methods can be used for the preparation of the preparation of the present invention. Additionally, in carrying out the preparation, other drug eliminating component or drug elimination accelerating component, stabilizing agent, an emulsifying agent, an osmotic pressure adjusting agent, a buffer agent, a isotonic agent, a flavoring, a preservative, a pH adjusting agent, a soothing agent, a coloring agent, an excipient, a binder, a lubricant, a disintegrating agent and the like other components can be formulated, as long as they do not exert bad influences on HA or a salt thereof and do not exert influences upon the effects of the present invention.

Although the preparation of the present invention can be produced in the aforementioned manner, a commercially available product containing HA or a salt thereof may be used directly as the preparation of the present invention Such a commercially available product includes for example, a mouth wash liquid "Kinusui" (registered trademark) (Seikagaku Corporation). The product is an aqueous solution of sodium HA and contains a flavoring (xylitol), preservatives (sodium benzoate and potassium sorbate) and pH adjusting agents (Sodium hydrogen phosphate and sodium dihydrogenphosphate) as other components. The mouth wash liquid "Kinusui" (registered trademark) (Seikagaku Corporation) can be used particularly preferably as the preparation of the present invention.

<3> Object for Application, Application Method and the Like of the Preparation of the Present Invention The preparation of the present invention can be used for the elimination of drugs from the surface of every matter. Thus, the matter as the object of drug elimination is not particularly limited, as long as the drug to be eliminated is already contacted therewith or adhered thereto and includes for example non-living beings (e.g., industrial parts, industrial products and the like), living beings (animals, plants and the like) and the like. Particularly, living being is preferable. Particularly, an animal tissue is preferable and an epithelial tissue is more preferable.

An example of the epithelial tissue includes epithelia of the inside of digestive organs (inside of the oral cavity, inside of the stomach, inside of the duodenum, inside of the small intestines, inside of the large intestines and the like), epithelia of the surface of various organs (the heart, the lungs, the liver, the spleen, the kidney and the like), epithelia of the skin and eyes, epithelia of the inside of various cavities (inside of the ear cavity, inside of the nose cavity and the like), epithelia of the inside of urinary organs (inside of a urethra, inside of the bladder and the like), epithelia of the inside of reproductive organs (inside of the vagina, inside of the womb and the like) and the like. The preparation of the present invention can be used for the elimination of drugs or acceleration of elimination of drugs from any one of these epithelia. As the epithelial tissues, mucosal epithelia are particularly preferable.

Although kinds and the like of the mucosal epithelia are not particularly limited too, the mucosal epithelia inside the digestive organs are preferable. The epithelium of oral cavity is more preferable.

The preparation of the present invention can be used with the object of eliminating drugs, or accelerating elimination of drugs, from the surface of these things. Additionally, since the preparation of the present invention exerts effect of eliminating drugs, or effect of accelerating elimination of drugs, from the surface of these things, it also exerts as a result to reduce existing amount and the like of drugs on the surface of these things. Accordingly, the term "an agent for eliminating a drug" as used herein also includes a conception as an agent which aim at exerting various effects generated by the drug elimination, such as "drug amount reducer", "drug concentration reducer" and the like. Additionally, the term "an agent for eliminating a drug" as used herein also includes a conception as various agents derived from drug elimination as the main purpose, such as "washes for drug elimination" on the surface of things and the like. Accordingly, the agent for eliminating a drug of the present invention also includes a conception as washes and the like which aim at eliminating drugs from various things, such as "mouth washes for drug elimination", "stomach washes for drug elimination", "eye washes for drug elimination" and the like, which contain HA or a salt thereof. In the same manner, the term "drug elimination accelerator" as used herein also includes a conception as agents which aim at exerting various effects derived from the drug elimination, such as "drug amount reduction accelerator", "drug concentration reduction accelerator" and the like. Additionally, the term "drug elimination accelerator" in the present invention also includes a conception as various agents derived with drug elimination acceleration as the main purpose, such as "washing accelerator for drug elimination" on the surface of things and the like. Accordingly, the accelerator of the present invention also includes a conception as washing acceleration and the like which aim at acceleration of eliminating drugs from various things, such as "mouth wash accelerator for drug elimination", "stomach wash accelerator for drug elimination", "eye wash accelerator for drug elimination" and the like, which contain HA or a salt thereof.

In this connection, the term "elimination" as used in the instant application documents includes not only complete elimination of a thing but also partial elimination thereof.

Although the drug as the object of elimination or acceleration of elimination by the preparation of the present invention is not particularly limited too, as long as that the drug is already contacted with or adhered to the aforementioned things and its elimination is expected at the application situation of the preparation of the present invention. An example of such an agent includes medicaments, reagents and the like, of which medicaments are preferable. Additionally, it is also preferable that the drug is an agent having steroid nucleus.

Method for using the agent for eliminating a drug of the present invention is not particularly limited, as long as that it is used based on such an embodiment that the molecule of HA or a salt thereof as the component of the agent for eliminating a drug of the present invention is contacted with the molecule of a drug contacted with or adhered to a thing (drug to be eliminated) and said drug is eliminated together with the agent for eliminating a drug of the present invention. It can be appropriately selected according to the things which become the objects of drug elimination, situations, purposes and the like.

For example, it may be used based on such an embodiment that a thing which becomes the object of drug elimination is soaked in the agent for eliminating a drug of the present invention, and then the agent for eliminating a drug of the present invention is separated. Alternatively, the agent for eliminating a drug of the present invention is poured or sprayed on the thing that becomes the object of drug elimination, or the thing that becomes the object of drug elimination and the agent for eliminating a drug of the present invention are allowed to contact with each other, followed by fluidizing the agent for eliminating a drug by agitation, shaking or the like physical stimulus.

For example, in order to eliminate a drug from inside of the oral cavity, the mouth is rinsed using the agent for eliminating a drug of the present invention and then the agent for eliminating a drug of the present invention is spit out. Thus, method for using the agent for eliminating a drug of the present invention can be appropriately set according to its purpose and the like.

A method for using the accelerator of the present invention is not particularly limited, as long as that it is used based on such an embodiment that the molecule of HA or a salt thereof as the component of the accelerator of the present invention is contacted with a thing that becomes the object of drug elimination acceleration, and said molecule of HA or a salt thereof is adhered to said thing. It can be appropriately selected according to the things that become the objects of drug elimination acceleration, cases, purposes and the like.

For example, a thing that becomes the object of drug elimination acceleration is soaked in the accelerator of the present invention. Alternatively, the accelerator of the present invention is poured or sprayed on the thing that becomes the object of drug elimination acceleration, or the thing that becomes the object of drug elimination acceleration and the accelerator of the present invention are allowed to contact with each other, followed by fluidizing the agent for eliminating a drug by agitation, shaking or the like physical stimulus.

For example, in order to accelerate drug elimination inside of the oral cavity, the mouth is rinsed using the accelerator of the present invention. Thus, method for using the accelerator of the present invention can be appropriately set according to its purpose and the like.

Additionally, when elimination of more many drugs is desired, the aforementioned procedures and operations may be carried out repeatedly.

In this connection, it is preferable to use the accelerator of the present invention prior to the application of the drug to be eliminated. Namely, it is preferable to use the accelerator of the present invention in advance, before said drug contacts with or adhered to the thing that becomes the object of drug elimination acceleration. By this, even when said drug is contacted with or adhered to said thing thereafter, this can be easily eliminated.

Using amount, using interval and the like per once of the preparation of the present invention are not particularly limited, since these are items which should be individually decided according to the things that become the object of drug elimination or things that become the object of drug elimination acceleration, cases, purposes and the like. For example, when it is necessary to eliminate more many drugs within a short period of time or it is necessary to apply the preparation of the present invention also within a short period of time, using amount of the preparation of the present invention per once may be increased or the aforementioned procedures and operations may be carried out within a short period of time repeatedly.

EXAMPLES

Although the following describes the present invention further illustratively based on Examples, the technical scope of the present invention is not restricted thereby. The present Examples are Examples in which a drug having steroid nucleus is eliminated from inside of the oral cavity using the preparation of the present invention.

(1) Materials, Subjects and the Like

Firstly, materials, subjects and the like used in the Examples are explained.

(1-1) The Following was Used as the Preparation of the Present Invention.

Sodium HA-containing aqueous solution (a mouth wash liquid Kinsui (registered trademark) (Seikagaku Corporation)) (to be referred to as "HA solution" hereinafter)

Purified water was used as the control. Additionally, the following substance was used for the treatment prior to the application of the drug.

Artificial saliva (Saliveht (trademark) (Teijin Pharma Limited)) (to be referred to as "HA non-containing solution" hereinafter)

(1-2) The Following was Used as the Drug that Becomes the Object of Elimination and Acceleration of Elimination.

Fluticasone propionate (Flutide (trademark) 100 Rotadisk (trademark) (Glaxo Smith Kline plc.)) (to be referred to as "FP" hereinafter)

(1-3) Subjects

Healthy 5 adult volunteers were selected. In this connection, these volunteers received sufficient explanation from a doctor based on a descriptive document, and after understanding the explanation, submitted a document on their own judgment stating that they approved the participation in the test. Additionally, the subjects did not take alcohols from the day before the test until completion of the test and stopped smoking during 1 hour before the test.

(2) Test Methods and Results

In order to demonstrate effect of drug elimination when the HA solution was used and influence on the drug elimination when inside the oral cavity was treated with the HA solution before applying the drug, all of the following tests 1 to 6 were carried out on all members of the subjects. In this connection, application of FP was carried out by directly applying the FP (dry powder) took out on powder papers. Also, the subjects were given attention not to inhale the FP applied into the oral cavity from the bronchus to the lungs.

Test 1: After rinsing inside of the oral cavity, inside of the oral cavity was dried by blowing air for 30 seconds with a dryer, and then FP (100 μg) was sparged to the oral cavity. Thereafter, rinsing of the mouth with looking upward (gargling) was carried out for 5 seconds and then rinsing of the mouth facing front (rinsing) was carried out for 5 seconds (these are regarded as once), respectively using 20 ml of purified water, which was repeated 5 times.

Test 2: After rinsing inside of the oral cavity, inside of the oral cavity was dried by blowing air for 30 seconds with a dryer, and then PP (100 μg) was sparged to the oral cavity. Thereafter, gargling was carried out for 5 seconds and then rinsing was carried out for 5 seconds (these are regarded as once), respectively using 20 ml of the HA solution, which was repeated 5 times.

Test 3: After rinsing inside of the oral cavity, the HA non-containing solution was sprayed, and then FP (100 μg) was sparged to the oral cavity. Thereafter, gargling was carried out for 5 seconds and then rinsing was carried out for 5 seconds (these are regarded as once), respectively using 20 ml of purified water, which was repeated 5 times.

Test 4: After rinsing inside of the oral cavity, the HA non-containing solution was sprayed, and then FP (100 μg) was sparged to the oral cavity. Thereafter, gargling was carried out for 5 seconds and then rinsing was carried out for 5 seconds (these are regarded as once), respectively using 20 ml of the HA solution, and which was repeated 5 times.

Test 5: After rinsing inside of the oral cavity, gargling was carried out for 5 seconds using 5 ml of the HA solution and then FP (100 μg) was sparged to the oral cavity. Thereafter, gargling was carried out for 5 seconds and then rinsing was carried out for 5 seconds (these are regarded as once), respectively using 20 ml of purified water, which was repeated 5 times.

Test 6: After rinsing inside of the oral cavity, gargling was carried out for 5 seconds using 5 ml of the HA solution and then FP (100 μg) was sparged to the oral cavity. Thereafter, gargling was carried out for 5 seconds and then rinsing was carried out for 5 seconds (these are regarded as once), respectively using 20 ml of the HA solution, which was repeated 5 times.

In each test, the liquids spat out after gargling and rinsing by each subject were recovered, and FP concentrations in said liquids were respectively measured. Measurement of the FP concentration was carried out using HPLC by the method described in "*Yakugaku Zasshi*", vol. 121, p. 233-237 (2001).

Figure 1B:
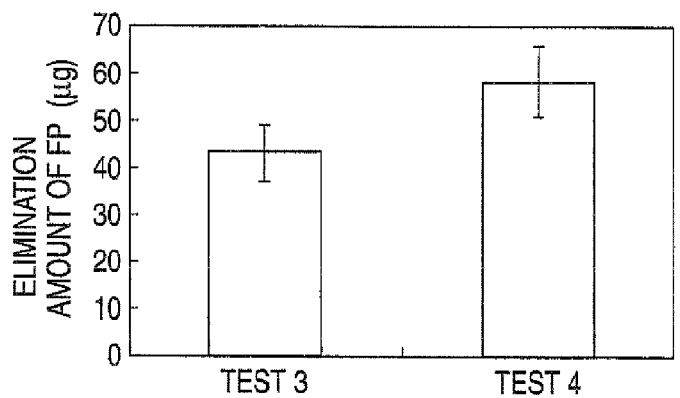
Figure 1C:
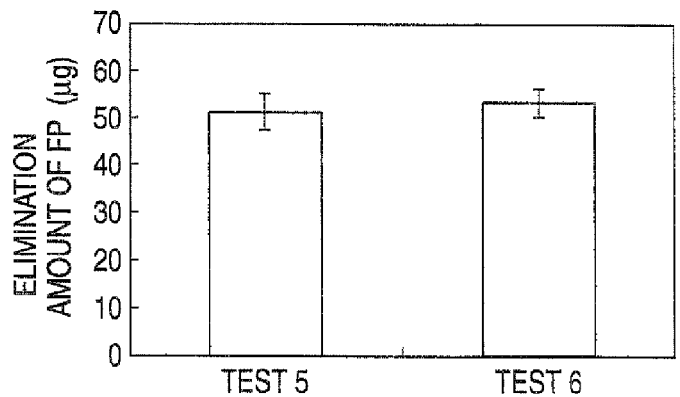
Figure 2D:
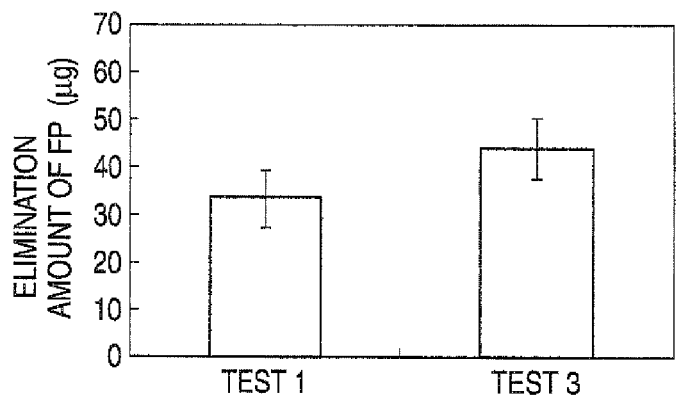
FIG. 2 is a graph which shows the amount of FP eliminated from inside of the oral cavity, and its comparison between each test.
Figure 2E:
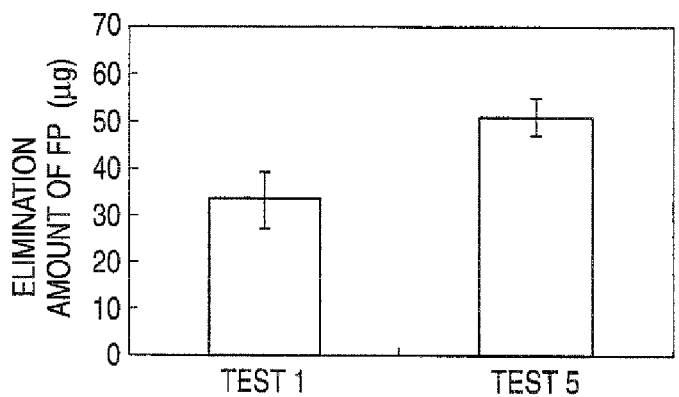
Figure 2F:
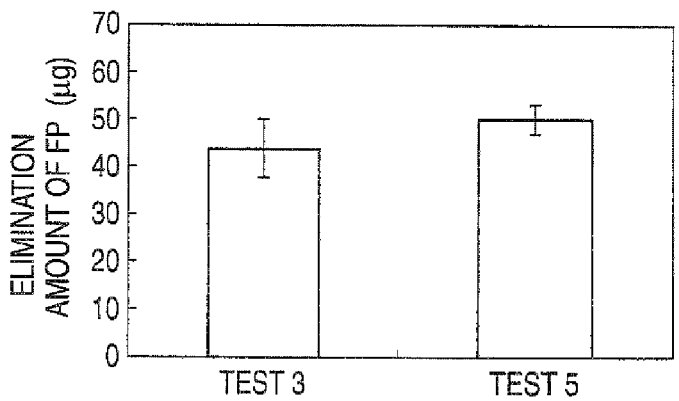
Figure 3G:
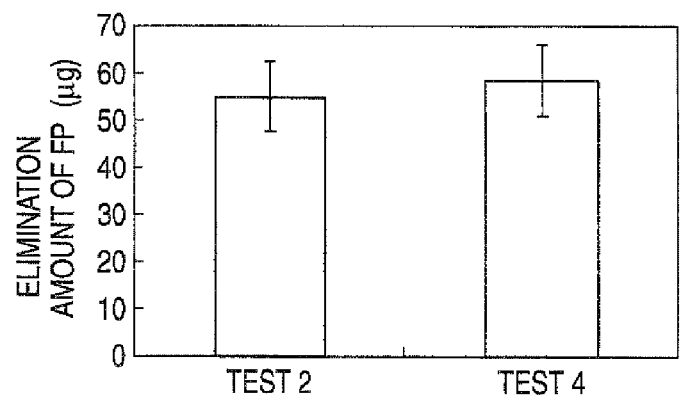
FIG. 3 is a graph which shows the amount of FP eliminated from inside of the oral cavity, and its comparison between each test.
Figure 3H:
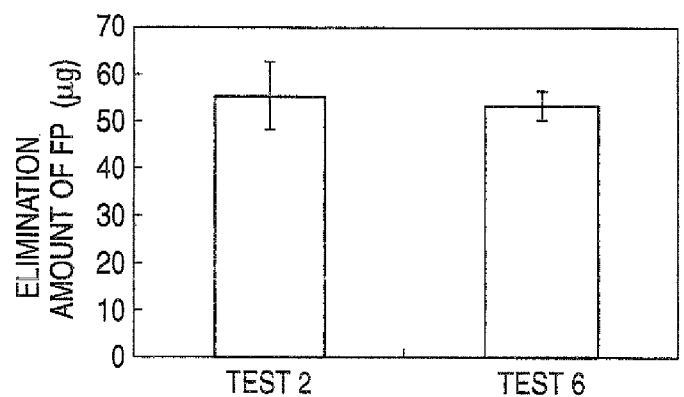
Figure 3I:
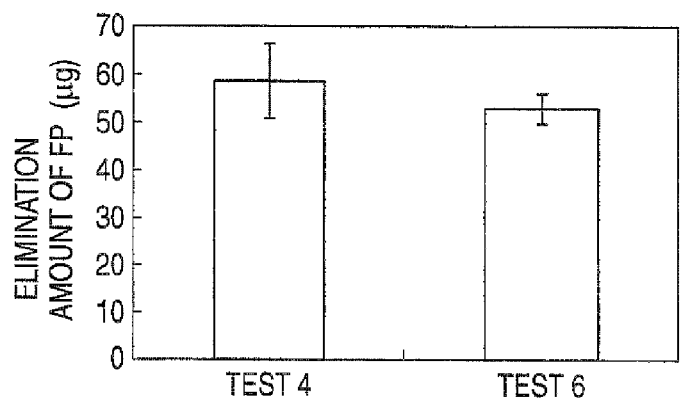

Based on the measured FP concentrations, amounts of FP eliminated from inside of the oral cavity were calculated, and mean value and standard deviation (SD) in each test were calculated. Results of comparing this between respective tests are shown in FIG. 1 to FIG. 3. In this connection, a statistically significant difference was found between the results of respective tests shown in FIG. 1A (Test 1 and Test 2) and B (Test 3 and Test 4), and FIG. 2D (Tests 1 and 3), E (Tests 1 and 5) and F (Tests 3 and 5) (t test; p<0.05).

It was shown by FIGS. 1A and B that the drug is eliminated more efficiently from the oral cavity epithelial tissue in comparison with the case of using water or the HA non-containing solution when inside of the oral cavity is rinsed by using the HA solution after application of the drug.

Also, it was shown by FIGS. 2D and E that when inside of the oral cavity is kept under a wet condition during sparge of the drug, elimination of the drug thereafter is further accelerated. It was shown also by FIG. 2F that the drug elimination acceleration effect is high in the HA solution in comparison with the HA non-containing solution.

Also, it was shown by FIG. 1C and FIG. 3G to I that the drug can be eliminated markedly efficiently when the HA solution is used at the time of either "sparge of the drug" or "elimination of the drug".

Additionally, when examination on the doctor's findings regarding diagnosis, subjective symptoms and objective symptoms, measurement of blood pressure, pulsation, body temperature and the like, and the like were carried out, it was confirmed that all members of the subjects showed no problem on each of the tests.

Based on the above results, it was shown that HA is markedly effective on both sides of the "elimination of drugs" and "acceleration of elimination", so that the effects and usefulness of the preparation of the present invention were confirmed.

While the present invention has been described in detail and with reference to specific embodiments thereof, it will be apparent to one skilled in the art that various changes and modifications can be made therein without departing from the scope thereof.

This application is based on Japanese patent application No. 2005-19835 filed on Jan. 27, 2005 and Japanese patent application No-2005-19836 filed on Jan. 27, 2005 and the entire contents thereof being hereby incorporated by reference.

Further, all references cited herein are incorporated in their entireties.

INDUSTRIAL APPLICABILITY

The preparation of the present invention can be utilized as an agent for eliminating an unnecessary drug and an agent for accelerating elimination of a drug.

The invention claimed is:

1. A method for eliminating a drug from the oral cavity of a human comprising:
  applying an agent for accelerating elimination of said drug, said agent comprising hyaluronic acid or a salt thereof, to the oral cavity from which said drug is to be eliminated;
  administering said drug; and
  eliminating said drug together with the agent by rinsing the oral cavity with water,
  wherein said drug to be eliminated is fluticasone propionate, and
  the agent comprising hyaluronic acid or a salt thereof is administered as a solution before the step of administering the fluticasone propionate.

* * * * *